(12) United States Patent
Jennewine (10) Patent No.: US 8,727,982 B2
(45) Date of Patent: May 20, 2014

(54) METHOD AND SYSTEM FOR PROVIDING INTEGRATED ANALYTE MONITORING AND INFUSION SYSTEM THERAPY MANAGEMENT

(75) Inventor: R. Curtis Jennewine, Winona Lake, IN (US)

(73) Assignee: Abbott Diabetes Care Inc., Alameda, CA (US)

( * ) Notice: Subject to any disclaimer, the term of this patent is extended or adjusted under 35 U.S.C. 154(b) by 145 days.

(21) Appl. No.: 13/532,346

(22) Filed: Jun. 25, 2012

(65) Prior Publication Data

US 2012/0265043 A1     Oct. 18, 2012

Related U.S. Application Data

(63) Continuation of application No. 11/462,974, filed on Aug. 7, 2006, now Pat. No. 8,206,296.

(51) Int. Cl.
*A61B 5/02*     (2006.01)
*A61B 5/145*     (2006.01)
*A61B 5/00*     (2006.01)

(52) U.S. Cl.
CPC ........... *A61B 5/14532* (2013.01); *A61B 5/4839* (2013.01); *A61M 2230/201* (2013.01)
USPC ....................................................... 600/365

(58) Field of Classification Search
CPC ............... A61B 5/145; A61B 5/14503; A61B 5/14532; A61B 5/1459; A61B 5/1468; A61B 5/1473; A61B 5/1486; A61B 5/14865; A61B 5/4839; A61B 5/483; A61M 2230/2016
USPC ......................................... 600/309, 345–366
See application file for complete search history.

(56) References Cited

U.S. PATENT DOCUMENTS

| | | |
|---|---|---|
| 3,208,121 A | 9/1965 | Price |
| 3,923,060 A | 12/1975 | Ellinwood, Jr. |
| 3,924,819 A | 12/1975 | Lapinskas |
| 4,003,379 A | 1/1977 | Ellinwood, Jr. |
| 4,055,175 A | 10/1977 | Clemens et al. |
| 4,076,182 A | 2/1978 | Stites |
| 4,151,845 A | 5/1979 | Clemens |
| 4,360,019 A | 11/1982 | Portner |
| 4,387,863 A | 6/1983 | Edmonston |
| 4,601,707 A | 7/1986 | Albisser et al. |
| 4,629,145 A | 12/1986 | Graham |
| 4,667,896 A | 5/1987 | Frey et al. |
| 4,685,903 A | 8/1987 | Cable et al. |
| 4,725,010 A | 2/1988 | Lotamer |

(Continued)

FOREIGN PATENT DOCUMENTS

| | | |
|---|---|---|
| AU | 2003/259741 | 2/2004 |
| CA | 2495648 | 2/2004 |

(Continued)

OTHER PUBLICATIONS

U.S. Appl. No. 11/462,974, Advisory Action mailed Feb. 10, 2012.

(Continued)

*Primary Examiner* — Navin Natnithithadha
(74) *Attorney, Agent, or Firm* — Jackson & Co., LLP (57) ABSTRACT

Method and system for providing diabetes management and insulin therapy based on substantially real time glucose monitoring system is provided.

18 Claims, 5 Drawing Sheets

(56) References Cited

U.S. PATENT DOCUMENTS

| | | |
|---|---|---|
| 4,802,638 A | 2/1989 | Burger et al. |
| 4,886,505 A | 12/1989 | Haynes et al. |
| 5,019,096 A | 5/1991 | Fox, Jr. et al. |
| 5,067,665 A | 11/1991 | LoStracco et al. |
| 5,097,834 A | 3/1992 | Skrabal |
| 5,109,577 A | 5/1992 | Young |
| 5,209,414 A | 5/1993 | Clemens et al. |
| 5,236,143 A | 8/1993 | Dragon |
| 5,237,993 A | 8/1993 | Skrabal |
| 5,250,023 A | 10/1993 | Lee |
| 5,266,359 A | 11/1993 | Spielvogel |
| 5,284,425 A | 2/1994 | Holtermann et al. |
| 5,344,411 A | 9/1994 | Domb et al. |
| 5,349,852 A | 9/1994 | Kamen et al. |
| 5,390,671 A | 2/1995 | Lord et al. |
| 5,437,656 A | 8/1995 | Shikani et al. |
| 5,451,424 A | 9/1995 | Solomon et al. |
| 5,515,390 A | 5/1996 | Benton |
| 5,526,844 A | 6/1996 | Kamen et al. |
| 5,533,389 A | 7/1996 | Kamen et al. |
| 5,558,640 A | 9/1996 | Pfeiler |
| 5,569,186 A | 10/1996 | Lord et al. |
| 5,593,852 A | 1/1997 | Heller et al. |
| 5,599,321 A | 2/1997 | Conway et al. |
| 5,601,435 A | 2/1997 | Quy |
| 5,662,904 A | 9/1997 | Ferguson et al. |
| 5,673,691 A | 10/1997 | Abrams et al. |
| 5,738,220 A | 4/1998 | Geszler |
| 5,807,375 A | 9/1998 | Gross et al. |
| 5,822,715 A | 10/1998 | Worthington et al. |
| 5,899,855 A | 5/1999 | Brown |
| 5,918,603 A | 7/1999 | Brown |
| 5,925,021 A | 7/1999 | Castellano et al. |
| 5,951,521 A | 9/1999 | Mastrototaro et al. |
| 5,954,643 A | 9/1999 | VanAntwerp et al. |
| 5,956,501 A | 9/1999 | Brown |
| 5,975,120 A | 11/1999 | Novosel |
| 5,987,353 A | 11/1999 | Khatchatrian et al. |
| 5,988,545 A | 11/1999 | King |
| 6,083,248 A | 7/2000 | Thompson |
| 6,134,461 A | 10/2000 | Say et al. |
| 6,175,752 B1 | 1/2001 | Say et al. |
| 6,233,539 B1 | 5/2001 | Brown |
| 6,247,664 B1 | 6/2001 | Peterson et al. |
| 6,248,067 B1 | 6/2001 | Causey et al. |
| 6,254,586 B1 | 7/2001 | Mann et al. |
| 6,284,478 B1 | 9/2001 | Heller et al. |
| 6,379,301 B1 | 4/2002 | Worthington et al. |
| 6,418,332 B1 | 7/2002 | Mastrototaro et al. |
| 6,427,088 B1 | 7/2002 | Bowman, IV et al. |
| 6,471,689 B1 | 10/2002 | Joseph et al. |
| 6,482,156 B2 | 11/2002 | Iliff |
| 6,484,045 B1 | 11/2002 | Holker et al. |
| 6,485,461 B1 | 11/2002 | Mason et al. |
| 6,498,043 B1 | 12/2002 | Schulman et al. |
| 6,554,798 B1 | 4/2003 | Mann et al. |
| 6,558,321 B1 | 5/2003 | Burd et al. |
| 6,562,001 B2 | 5/2003 | Lebel et al. |
| 6,564,105 B2 | 5/2003 | Starkweather et al. |
| 6,571,128 B2 | 5/2003 | Lebel et al. |
| 6,572,542 B1 * | 6/2003 | Houben et al. ................ 600/300 |
| 6,576,101 B1 | 6/2003 | Heller et al. |
| 6,577,899 B2 | 6/2003 | Lebel et al. |
| 6,585,644 B2 | 7/2003 | Lebel et al. |
| 6,598,824 B2 | 7/2003 | Schmidt |
| 6,635,014 B2 | 10/2003 | Starkweather et al. |
| 6,641,562 B1 | 11/2003 | Peterson |
| 6,648,821 B2 | 11/2003 | Lebel et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,692,457 B2 | 2/2004 | Flaherty |
| 6,694,191 B2 | 2/2004 | Starkweather et al. |
| 6,699,218 B2 | 3/2004 | Flaherty et al. |
| 6,702,857 B2 | 3/2004 | Brauker et al. |
| 6,723,072 B2 | 4/2004 | Flaherty et al. |
| 6,733,446 B2 | 5/2004 | Lebel et al. |
| 6,736,797 B1 | 5/2004 | Larsen et al. |
| 6,740,059 B2 | 5/2004 | Flaherty |
| 6,740,075 B2 | 5/2004 | Lebel et al. |
| 6,741,877 B1 | 5/2004 | Shults et al. |
| 6,744,350 B2 | 6/2004 | Blomquist |
| 6,749,587 B2 | 6/2004 | Flaherty |
| 6,758,810 B2 | 7/2004 | Lebel et al. |
| 6,768,425 B2 | 7/2004 | Flaherty et al. |
| 6,789,195 B1 | 9/2004 | Prihoda et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,830,558 B2 | 12/2004 | Flaherty et al. |
| 6,837,858 B2 | 1/2005 | Cunningham et al. |
| 6,852,104 B2 | 2/2005 | Blomquist |
| 6,862,465 B2 | 3/2005 | Shults et al. |
| 6,873,268 B2 | 3/2005 | Lebel et al. |
| 6,882,940 B2 | 4/2005 | Potts et al. |
| 6,887,270 B2 | 5/2005 | Miller et al. |
| 6,896,666 B2 | 5/2005 | Kochamaba |
| 6,902,207 B2 | 6/2005 | Lickliter |
| 6,916,159 B2 | 7/2005 | Rush et al. |
| 6,923,763 B1 * | 8/2005 | Kovatchev et al. ........... 600/300 |
| 6,931,327 B2 | 8/2005 | Goode, Jr. et al. |
| 6,936,006 B2 | 8/2005 | Sabra |
| 6,946,446 B2 | 9/2005 | Ma et al. |
| 6,950,708 B2 | 9/2005 | Bowman, IV et al. |
| 6,958,705 B2 | 10/2005 | Lebel et al. |
| 6,960,192 B1 | 11/2005 | Flaherty et al. |
| 6,974,437 B2 | 12/2005 | Lebel et al. |
| 7,003,336 B2 | 2/2006 | Holker et al. |
| 7,018,360 B2 | 3/2006 | Flaherty et al. |
| 7,024,245 B2 | 4/2006 | Lebel et al. |
| 7,029,455 B2 | 4/2006 | Flaherty |
| 7,034,677 B2 | 4/2006 | Steinthal et al. |
| 7,052,251 B2 | 5/2006 | Nason et al. |
| 7,052,472 B1 | 5/2006 | Miller et al. |
| 7,066,922 B2 | 6/2006 | Angel et al. |
| 7,074,307 B2 | 7/2006 | Simpson et al. |
| 7,077,328 B2 | 7/2006 | Krishnaswamy et al. |
| 7,079,977 B2 | 7/2006 | Osorio et al. |
| 7,081,195 B2 | 7/2006 | Simpson et al. |
| 7,108,778 B2 | 9/2006 | Simpson et al. |
| 7,110,803 B2 | 9/2006 | Shults et al. |
| 7,134,999 B2 | 11/2006 | Brauker et al. |
| 7,136,689 B2 | 11/2006 | Shults et al. |
| 7,137,964 B2 | 11/2006 | Flaherty |
| 7,144,384 B2 | 12/2006 | Gorman et al. |
| 7,155,112 B2 | 12/2006 | Uno et al. |
| 7,167,818 B2 | 1/2007 | Brown |
| 7,171,274 B2 | 1/2007 | Starkweather et al. |
| 7,171,312 B2 | 1/2007 | Steinthal et al. |
| 7,192,450 B2 | 3/2007 | Brauker et al. |
| 7,207,974 B2 | 4/2007 | Safabash et al. |
| 7,226,278 B2 | 6/2007 | Nason et al. |
| 7,226,978 B2 | 6/2007 | Tapsak et al. |
| 7,229,042 B2 | 6/2007 | Thebault et al. |
| 7,267,665 B2 | 9/2007 | Steil et al. |
| 7,276,029 B2 | 10/2007 | Goode, Jr. et al. |
| 7,303,549 B2 | 12/2007 | Flaherty et al. |
| 7,310,544 B2 | 12/2007 | Brister et al. |
| 7,318,816 B2 | 1/2008 | Bobroff et al. |
| 7,324,012 B2 | 1/2008 | Mann et al. |
| 7,329,239 B2 | 2/2008 | Safabash et al. |
| 7,335,294 B2 | 2/2008 | Heller et al. |
| 7,354,420 B2 | 4/2008 | Steil et al. |
| 7,364,568 B2 | 4/2008 | Angel et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,402,153 B2 | 7/2008 | Steil et al. |
| 7,404,796 B2 | 7/2008 | Ginsberg |

(56) References Cited

U.S. PATENT DOCUMENTS

| | | |
|---|---|---|
| 7,424,318 B2 | 9/2008 | Brister et al. |
| 7,429,258 B2 | 9/2008 | Angel et al. |
| 7,455,663 B2 | 11/2008 | Bikovsky |
| 7,460,898 B2 | 12/2008 | Brister et al. |
| 7,462,264 B2 | 12/2008 | Heller et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,519,408 B2 | 4/2009 | Rasdal et al. |
| 7,547,281 B2 | 6/2009 | Hayes et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,645,263 B2 | 1/2010 | Angel et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,697,967 B2 | 4/2010 | Stafford |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,147 B1 | 6/2010 | Osorio et al. |
| 7,731,657 B2 | 6/2010 | Stafford |
| 7,736,344 B2 | 6/2010 | Moberg et al. |
| 7,763,042 B2 | 7/2010 | Iio et al. |
| 7,822,454 B1 | 10/2010 | Alden et al. |
| RE43,316 E * | 4/2012 | Brown et al. .......... 600/309 |
| 2002/0016719 A1 | 2/2002 | Nemeth et al. |
| 2002/0019612 A1 | 2/2002 | Watanabe et al. |
| 2002/0106709 A1 | 8/2002 | Potts et al. |
| 2002/0107476 A1 | 8/2002 | Mann et al. |
| 2002/0147135 A1 | 10/2002 | Schnell |
| 2002/0169439 A1 | 11/2002 | Flaherty et al. |
| 2002/0193679 A1 | 12/2002 | Malave et al. |
| 2003/0023317 A1 | 1/2003 | Brauker et al. |
| 2003/0032874 A1 | 2/2003 | Rhodes et al. |
| 2003/0055380 A1 | 3/2003 | Flaherty et al. |
| 2003/0060753 A1 | 3/2003 | Starkweather et al. |
| 2003/0065308 A1 | 4/2003 | Lebel et al. |
| 2003/0069541 A1 | 4/2003 | Gillis et al. |
| 2003/0073414 A1 | 4/2003 | P. Capps |
| 2003/0114836 A1 | 6/2003 | Estes et al. |
| 2003/0122021 A1 | 7/2003 | McConnell et al. |
| 2003/0130616 A1 | 7/2003 | Steil et al. |
| 2003/0144362 A1 | 7/2003 | Utterberg et al. |
| 2003/0167035 A1 | 9/2003 | Flaherty et al. |
| 2003/0175323 A1 | 9/2003 | Utterberg et al. |
| 2003/0176933 A1 | 9/2003 | Lebel et al. |
| 2003/0212379 A1 | 11/2003 | Bylund et al. |
| 2003/0217966 A1 | 11/2003 | Tapsak et al. |
| 2003/0225361 A1 | 12/2003 | Sabra |
| 2004/0010207 A1 | 1/2004 | Flaherty et al. |
| 2004/0011671 A1 | 1/2004 | Shults et al. |
| 2004/0015131 A1 | 1/2004 | Flaherty et al. |
| 2004/0041749 A1 | 3/2004 | Dixon |
| 2004/0045879 A1 | 3/2004 | Shults et al. |
| 2004/0064088 A1 | 4/2004 | Gorman et al. |
| 2004/0064096 A1 | 4/2004 | Flaherty et al. |
| 2004/0122530 A1 | 6/2004 | Hansen et al. |
| 2004/0133390 A1 | 7/2004 | Osorio et al. |
| 2004/0135684 A1 | 7/2004 | Steinthal et al. |
| 2004/0153032 A1 | 8/2004 | Garribotto et al. |
| 2004/0155770 A1 | 8/2004 | Nelson et al. |
| 2004/0167464 A1 | 8/2004 | Ireland et al. |
| 2004/0186362 A1 | 9/2004 | Brauker et al. |
| 2004/0193025 A1 | 9/2004 | Steil et al. |
| 2004/0193090 A1 | 9/2004 | Lebel et al. |
| 2004/0199059 A1 | 10/2004 | Brauker et al. |
| 2004/0210180 A1 | 10/2004 | Altman |
| 2004/0210208 A1 | 10/2004 | Paul et al. |
| 2004/0225338 A1 | 11/2004 | Lebel et al. |
| 2004/0254433 A1 | 12/2004 | Bandis et al. |
| 2005/0004439 A1 | 1/2005 | Shin et al. |
| 2005/0010269 A1 | 1/2005 | Lebel et al. |
| 2005/0027180 A1 | 2/2005 | Goode, Jr. et al. |
| 2005/0031689 A1 | 2/2005 | Shults et al. |
| 2005/0038332 A1 | 2/2005 | Saidara et al. |
| 2005/0038674 A1 | 2/2005 | Braig et al. |
| 2005/0043598 A1 | 2/2005 | Goode, Jr. et al. |
| 2005/0065464 A1 | 3/2005 | Talbot et al. |
| 2005/0090607 A1 | 4/2005 | Tapsak et al. |
| 2005/0096511 A1 | 5/2005 | Fox et al. |
| 2005/0112169 A1 | 5/2005 | Brauker et al. |
| 2005/0113653 A1 | 5/2005 | Fox et al. |
| 2005/0119540 A1 | 6/2005 | Potts et al. |
| 2005/0143635 A1 | 6/2005 | Kamath et al. |
| 2005/0171512 A1 | 8/2005 | Flaherty |
| 2005/0176136 A1 | 8/2005 | Burd et al. |
| 2005/0181010 A1 | 8/2005 | Hunter et al. |
| 2005/0182306 A1 | 8/2005 | Sloan |
| 2005/0182358 A1 | 8/2005 | Veit et al. |
| 2005/0182366 A1 | 8/2005 | Vogt et al. |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0203461 A1 | 9/2005 | Flaherty et al. |
| 2005/0238507 A1 | 10/2005 | DiIanni et al. |
| 2005/0245795 A1 | 11/2005 | Goode, Jr. et al. |
| 2005/0245799 A1 | 11/2005 | Brauker et al. |
| 2005/0261667 A1 | 11/2005 | Crank et al. |
| 2005/0277872 A1 | 12/2005 | Colby et al. |
| 2006/0001551 A1 | 1/2006 | Kraft et al. |
| 2006/0004603 A1 | 1/2006 | Peterka et al. |
| 2006/0010098 A1 | 1/2006 | Goodnow et al. |
| 2006/0015020 A1 | 1/2006 | Neale et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0041229 A1 | 2/2006 | Garibotto et al. |
| 2006/0065772 A1 | 3/2006 | Grant et al. |
| 2006/0079740 A1 | 4/2006 | Silver et al. |
| 2006/0095020 A1 | 5/2006 | Casas et al. |
| 2006/0154642 A1 | 7/2006 | Scannell |
| 2006/0166629 A1 | 7/2006 | Reggiardo |
| 2006/0173406 A1 | 8/2006 | Hayes et al. |
| 2006/0173444 A1 | 8/2006 | Choy et al. |
| 2006/0173712 A1 | 8/2006 | Joubert |
| 2006/0178633 A1 | 8/2006 | Garibotto et al. |
| 2006/0189863 A1 | 8/2006 | Peyser et al. |
| 2006/0222566 A1 | 10/2006 | Brauker et al. |
| 2006/0224141 A1 | 10/2006 | Rush et al. |
| 2006/0226985 A1 | 10/2006 | Goodnow et al. |
| 2006/0247508 A1 | 11/2006 | Fennell |
| 2006/0282290 A1 | 12/2006 | Flaherty et al. |
| 2006/0293577 A1 | 12/2006 | Morrison et al. |
| 2007/0016381 A1 | 1/2007 | Kamath et al. |
| 2007/0027381 A1 | 2/2007 | Stafford |
| 2007/0060869 A1 | 3/2007 | Tolle et al. |
| 2007/0060870 A1 | 3/2007 | Tolle et al. |
| 2007/0060871 A1 | 3/2007 | Istoc et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078818 A1 | 4/2007 | Zivitz et al. |

(56) References Cited

U.S. PATENT DOCUMENTS

| | | |
|---|---|---|
| 2007/0093786 A1 | 4/2007 | Goldsmith et al. |
| 2007/0100222 A1 | 5/2007 | Mastrototaro et al. |
| 2007/0106135 A1 | 5/2007 | Sloan et al. |
| 2007/0118405 A1 | 5/2007 | Campbell et al. |
| 2007/0128682 A1 | 6/2007 | Rosman et al. |
| 2007/0129621 A1 | 6/2007 | Kellogg et al. |
| 2007/0149875 A1 | 6/2007 | Ouyang et al. |
| 2007/0163880 A1 | 7/2007 | Woo et al. |
| 2007/0191702 A1 | 8/2007 | Yodfat et al. |
| 2007/0203407 A1 | 8/2007 | Hoss et al. |
| 2007/0203966 A1 | 8/2007 | Brauker et al. |
| 2007/0208246 A1 | 9/2007 | Brauker et al. |
| 2007/0213657 A1 | 9/2007 | Jennewine et al. |
| 2007/0219480 A1 | 9/2007 | Kamen et al. |
| 2007/0219597 A1 | 9/2007 | Kamen et al. |
| 2007/0228071 A1 | 10/2007 | Kamen et al. |
| 2007/0235331 A1 | 10/2007 | Simpson et al. |
| 2007/0249922 A1 | 10/2007 | Peyser et al. |
| 2007/0255114 A1 | 11/2007 | Ackermann et al. |
| 2007/0282299 A1 | 12/2007 | Hellwig |
| 2007/0299409 A1 | 12/2007 | Whitbourne et al. |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0018480 A1 | 1/2008 | Sham |
| 2008/0021666 A1 | 1/2008 | Goode, Jr. et al. |
| 2008/0033254 A1 | 2/2008 | Kamath et al. |
| 2008/0033268 A1 | 2/2008 | Stafford |
| 2008/0039702 A1 | 2/2008 | Hayter et al. |
| 2008/0045824 A1 | 2/2008 | Tapsak et al. |
| 2008/0064937 A1 | 3/2008 | McGarraugh et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0093447 A1 | 4/2008 | Johnson et al. |
| 2008/0097246 A1 | 4/2008 | Stafford |
| 2008/0108942 A1 | 5/2008 | Brister et al. |
| 2008/0119707 A1 | 5/2008 | Stafford |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200897 A1 | 8/2008 | Hoss et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0242961 A1 | 10/2008 | Brister et al. |
| 2008/0262469 A1 | 10/2008 | Brister et al. |
| 2008/0269687 A1 | 10/2008 | Chong et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0006133 A1 | 1/2009 | Weinert et al. |
| 2009/0012379 A1 | 1/2009 | Goode, Jr. et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0062633 A1 | 3/2009 | Brauker et al. |
| 2009/0062635 A1 | 3/2009 | Brauker et al. |
| 2009/0069650 A1 | 3/2009 | Jennewine et al. |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Kamath et al. |
| 2009/0088614 A1 | 4/2009 | Taub |
| 2009/0088787 A1 | 4/2009 | Koike et al. |
| 2009/0099436 A1 | 4/2009 | Brister et al. |
| 2009/0102678 A1 | 4/2009 | Mazza et al. |
| 2009/0105560 A1 | 4/2009 | Solomon |
| 2009/0105569 A1 | 4/2009 | Stafford |
| 2009/0124877 A1 | 5/2009 | Goode, Jr. et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Le et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0253973 A1 | 10/2009 | Bashan et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |

(56) References Cited

U.S. PATENT DOCUMENTS

| | | | |
|---|---|---|---|
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0063373 A1 | 3/2010 | Kamath et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0119693 A1 | 5/2010 | Tapsak et al. |
| 2010/0121169 A1 | 5/2010 | Petisce et al. |
| 2010/0292634 A1 | 11/2010 | Kircher et al. |
| 2010/0312176 A1 | 12/2010 | Lauer et al. |

FOREIGN PATENT DOCUMENTS

| | | |
|---|---|---|
| CA | 2498682 | 9/2005 |
| CA | 2555749 | 9/2005 |
| CA | 2632709 | 6/2007 |
| CA | 2615575 | 6/2008 |
| CA | 2701374 | 4/2009 |
| EP | 1956371 | 8/2008 |
| EP | 2260757 | 12/2010 |
| WO | WO-01/52935 | 7/2001 |
| WO | WO-01/54753 | 8/2001 |
| WO | WO-2004/015539 | 2/2004 |
| WO | WO-2006/037109 | 4/2006 |
| WO | WO-2007/065285 | 6/2007 |
| WO | WO-2007/101260 | 9/2007 |
| WO | WO-2007/149319 | 12/2007 |
| WO | WO-2008/001366 | 1/2008 |
| WO | WO-2008/003003 | 1/2008 |
| WO | WO-2008/005780 | 1/2008 |
| WO | WO-2011/104616 | 9/2011 |

OTHER PUBLICATIONS

U.S. Appl. No. 11/462,974, Notice of Allowance mailed Mar. 14, 2012.

U.S. Appl. No. 11/462,974, Office Action mailed Feb. 16, 2011.

U.S. Appl. No. 11/462,974, Office Action mailed Oct. 27, 2011.

* cited by examiner

METHOD AND SYSTEM FOR PROVIDING INTEGRATED ANALYTE MONITORING AND INFUSION SYSTEM THERAPY MANAGEMENT

RELATED APPLICATION

The present application is a continuation of U.S. patent application Ser. No. 11/462,974 filed Aug. 7, 2006, issued as U.S. Pat. No. 8,206,296 on Jun. 26, 2012, entitled "Method and System for Providing Integrated Analyte Monitoring and Infusion System Therapy Management", the disclosure of which is incorporated herein by reference for all purposes.

BACKGROUND

With increasing use of pump therapy for Type 1 diabetic patients, young and old alike, the importance of controlling the infusion device such as external infusion pumps is evident. Indeed, presently available external infusion devices typically include an input mechanism such as buttons through which the patient may program and control the infusion device. Such infusion devices also typically include a user interface such as a display which is configured to display information relevant to the patient's infusion progress, status of the various components of the infusion device, as well as other programmable information such as patient specific basal profiles.

The external infusion devices are typically connected to an infusion set which includes a cannula that is placed transcutaneously through the skin of the patient to infuse a select dosage of insulin based on the infusion device's programmed basal rates or any other infusion rates as prescribed by the patient's doctor. Generally, the patient is able to control the pump to administer additional doses of insulin during the course of wearing and operating the infusion device such as for, administering a carbohydrate bolus prior to a meal. Certain infusion devices include food database that has associated therewith, an amount of carbohydrate, so that the patient may better estimate the level of insulin dosage needed for, for example, calculating a bolus amount.

However, in general, most estimation or calculation of a bolus amount for administration, or a determination of a suitable basal profile, for that matter, are educated estimates based on the patient's physiology as determined by the patient's doctor, or an estimate performed by the patient. Moreover, the infusion devices do not generally include enhancement features that would better assist the diabetic patients to control and/or manage the glucose levels.

In view of the foregoing, it would be desirable to have a method and system for providing insulin therapy determination and recommendation based on real time monitored analyte levels of the patient for proactive insulin therapy treatment to improve management of diabetes.

SUMMARY OF THE INVENTION

In accordance with the various embodiments of the present invention, there are provided method and system for receiving data associated with monitored analyte related levels for a predetermined time period substantially in real time, retrieving one or more therapy profiles associated with the monitored analyte related levels, generating one or more modifications to the retrieved one or more therapy profiles based on the data associated with the monitored analyte related levels.

These and other objects, features and advantages of the present invention will become more fully apparent from the following detailed description of the embodiments, the appended claims and the accompanying drawings.

DETAILED DESCRIPTION

As described in detail below, in accordance with the various embodiments of the present invention, there are provided various embodiments for providing real time or substantially real time monitored levels associated with a patient's analyte levels, and one or more associated therapy recommendation associated with the monitored analyte levels to provide real time insulin therapy and management. Accordingly, in one embodiment of the present invention, diabetic patients may better control the glucose levels and improve their physiological conditions based on accurate and substantially real time monitoring of glucose levels, and are provided with one or more recommendations for modifying or maintaining the insulin therapy (based on, for example, insulin pump therapy), for real time proactive management of glucose levels.

Figure 1:
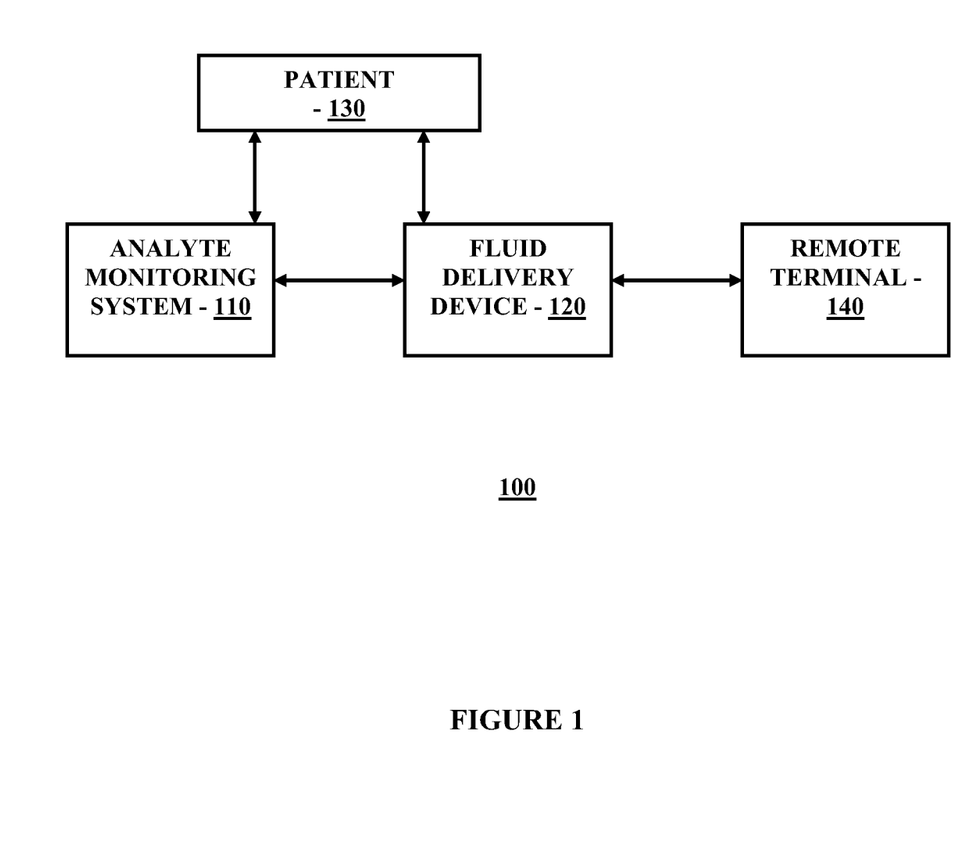
FIG. 1 is a block diagram illustrating an insulin therapy management system in accordance with one embodiment of the present invention.

FIG. 1 is a block diagram illustrating an insulin therapy management system for practicing one embodiment of the present invention. Referring to FIG. 1, the therapy management system 100 includes an analyte monitoring system 110 operatively coupled to a fluid delivery device 120, which may be in turn, operatively coupled to a remote terminal 140. As shown in the Figure, the analyte monitoring system 110 is, in one embodiment, coupled to the patient 130 so as to monitor or measure the analyte levels of the patient. Moreover, the fluid delivery device 120 is coupled to the patient using, for example, an infusion set and tubing connected to a cannula (not shown) that is placed transcutaneously through the skin of the patient so as to infuse medication such as, for example, insulin, to the patient.

Referring to FIG. 1, in one embodiment the analyte monitoring system 110 in one embodiment may include one or more analyte sensors subcutaneously positioned such that at least a portion of the analyte sensors are maintained in fluid contact with the patient's analytes. The analyte sensors may include, but are not limited to short term subcutaneous analyte sensors or transdermal analyte sensors, for example, which are configured to detect analyte levels of a patient over a predetermined time period, and after which, a replacement of the sensors is necessary.

The one or more analyte sensors of the analyte monitoring system 110 is coupled to a respective one or more of a data transmitter unit which is configured to receive one or more signals from the respective analyte sensors corresponding to the detected analyte levels of the patient, and to transmit the information corresponding to the detected analyte levels to a receiver device, and/or fluid delivery device 120. That is, over a communication link, the transmitter units may be configured to transmit data associated with the detected analyte levels periodically, and/or intermittently and repeatedly to one or more other devices such as the insulin delivery device and/or the remote terminal 140 for further data processing and analysis.

The transmitter units of the analyte monitoring system 110 may in one embodiment, be configured to transmit the analyte related data substantially in real time to the fluid delivery device 120 and/or the remote terminal 140 after receiving it from the corresponding analyte sensors such that the analyte level such as glucose level of the patient 130 may be monitored in real time. In one aspect, the analyte levels of the patient may be obtained using one or more discrete blood glucose testing devices such as blood glucose meters, or continuous analyte monitoring systems such as continuous glucose monitoring systems.

Additional analytes that may be monitored, determined or detected by the analyte monitoring system 110 include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined.

Moreover, within the scope of the present invention, the transmitter units of the analyte monitoring system 110 may be configured to directly communicate with one or more of the remote terminal 140 or the fluid delivery device 120. Furthermore, within the scope of the present invention, additional devices may be provided for communication in the analyte monitoring system 110 including additional receiver/data processing unit, remote terminals (such as a physician's terminal and/or a bedside terminal in a hospital environment, for example. In addition, within the scope of the present invention, one or more of the analyte monitoring system 110, the fluid delivery device 120 and the remote terminal 140 may be configured to communicate over a wireless data communication link such as, but not limited to a radio frequency (RF) communication link, Bluetooth® communication link, infrared communication link, or any other type of suitable wireless communication connection between two or more electronic devices, which may further be uni-directional or bi-directional communication between the two or more devices. Alternatively, the data communication link may include wired cable connection such as, for example, but not limited to RS232 connection, USB connection, or serial cable connection.

Referring back to FIG. 1, in one embodiment, the analyte monitoring system 110 includes a strip port configured to receive a test strip for capillary blood glucose testing. In one aspect, the glucose level measured using the test strip may in addition, be configured to provide periodic calibration of the analyte sensors of the analyte monitoring system 110 to assure and improve the accuracy of the analyte levels detected by the analyte sensors.

Additional detailed description of the continuous analyte monitoring system, its various components including the functional descriptions of the sensor, transmitter unit, receiver unit, and remote terminal/data processing terminal are provided in U.S. Pat. No. 6,175,752 issued Jan. 16, 2001 entitled "Analyte Monitoring Device and Methods of Use", and in application Ser. No. 10/745,878 filed Dec. 26, 2003, issued as U.S. Pat. No. 7,811,231, entitled "Continuous Glucose Monitoring System and Methods of Use", each assigned to the Assignee of the present application.

Referring again to FIG. 1, the fluid delivery device 120 may include in one embodiment, but not limited to, an external infusion device such as an external insulin infusion pump, an implantable pump, a pen-type insulin injector device, an on-body patch pump, an inhalable infusion device for nasal insulin delivery, or any other type of suitable delivery system. In addition, the remote terminal 140 in one embodiment may include for example, a desktop computer terminal, a data communication enabled kiosk, a laptop computer, a handheld computing device such as a personal digital assistant (PDAs), or a data communication enabled mobile telephone.

Figure 2:
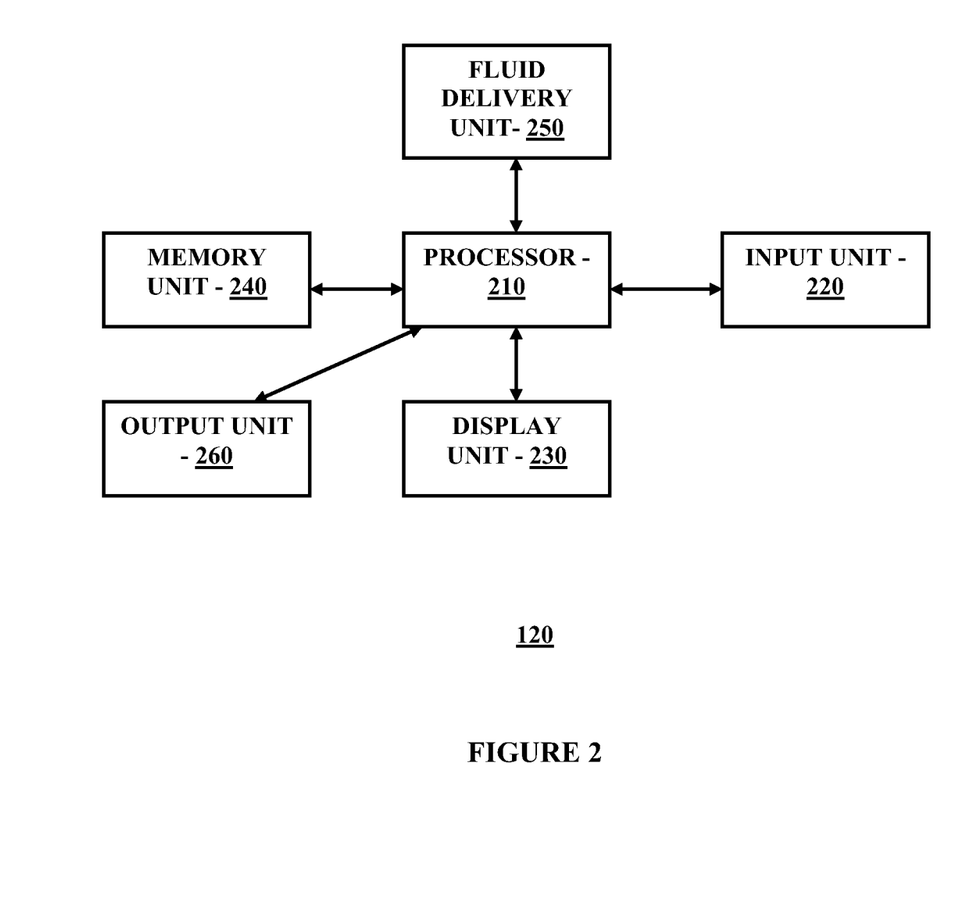
FIG. 2 is a block diagram illustrating the therapeutic fluid delivery device of FIG. 1 in accordance with one embodiment of the present invention.

FIG. 2 is a block diagram of an insulin delivery device of FIG. 1 in one embodiment of the present invention. Referring to FIG. 2, the fluid delivery device 120 in one embodiment includes a processor 210 operatively coupled to a memory unit 240, an input unit 220, a display unit 230, an output unit 260, and a fluid delivery unit 250. In one embodiment, the processor 210 includes a microprocessor that is configured to and capable of controlling the functions of the fluid delivery device 120 by controlling and/or accessing each of the various components of the fluid delivery device 120. In one embodiment, multiple processors may be provided as a safety measure and to provide redundancy in case of a single processor failure. Moreover, processing capabilities may be shared between multiple processor units within the insulin delivery device 120 such that pump functions and/or control may be performed faster and more accurately.

Referring back to FIG. 2, the input unit 220 operatively coupled to the processor 210 may include a jog dial, key pad buttons, a touch pad screen, or any other suitable input mechanism for providing input commands to the fluid delivery device 120. More specifically, in case of a jog dial input device, or a touch pad screen, for example, the patient or user of the fluid delivery device 120 will manipulate the respective jog dial or touch pad in conjunction with the display unit 230 which performs as both a data input and output units. The display unit 230 may include a touch sensitive screen, an LCD screen, or any other types of suitable display unit for the fluid delivery device 120 that is configured to display alphanumeric data as well as pictorial information such as icons associated with one or more predefined states of the fluid delivery device 120, or graphical representation of data such as trend charts and graphs associated with the insulin infusion rates, trend data of monitored glucose levels over a period of time, or textual notification to the patients.

Referring to FIG. 2, the output unit 260 operatively coupled to the processor 210 may include audible alarm including one or more tones and/or preprogrammed or programmable tunes or audio clips, or vibratory alert features having one or more pre-programmed or programmable vibratory alert levels. In one embodiment, the vibratory alert may also assist in priming the infusion tubing to minimize the potential for air or other undesirable material in the infusion tubing. Also shown in FIG. 2 is the fluid delivery unit 250 which is operatively coupled to the processor 210 and configured to deliver the insulin doses or amounts to the patient from the insulin reservoir or any other types of suitable containment for insulin to be delivered (not shown) in the fluid delivery device 120 via an infusion set coupled to a subcutaneously positioned cannula under the skin of the patient.

Referring yet again to FIG. 2, the memory unit 240 may include one or more of a random access memory (RAM), read only memory (ROM), or any other types of data storage units that is configured to store data as well as program instructions for access by the processor 210 and execution to control the fluid delivery device 120 and/or to perform data processing based on data received from the analyte monitoring system 110, the remote terminal 140, the patient 130 or any other data input source.

Figure 3:
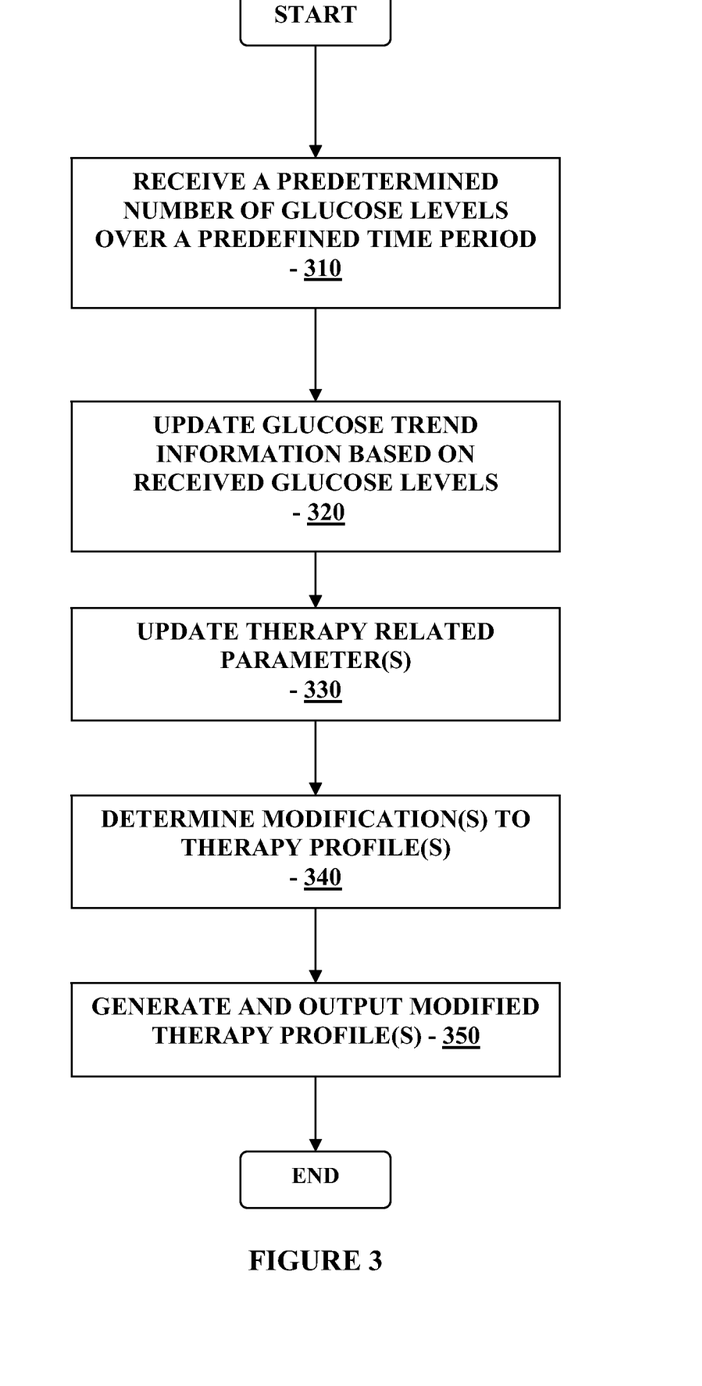
FIG. 3 is a flow chart illustrating a therapy management procedure based on real time monitored analyte levels in accordance with one embodiment of the present invention.

FIG. 3 is a flow chart illustrating insulin therapy management procedure based on real time monitored analyte levels in accordance with one embodiment of the present invention. Referring to FIG. 3, in one embodiment of the present invention, a predetermined number of consecutive glucose levels are received or detected over a predetermined or defined time period (310). For example, in one embodiment, referring to FIG. 1, the monitored glucose levels of a patient is substantially continuously received or detected substantially in real time for a predetermined time period. In one embodiment, the predefined time period may include one or more time periods, the data within which may provide a therapeutically meaningful basis for associated data analysis.

That is, the predefined time period of the real time monitored glucose data in one embodiment may include one or more time periods sufficient to provide glucose trend information or sufficient to provide analysis of glucose levels to adjust insulin therapy on an on-going, and substantially real time basis. For example, the predefined time period in one embodiment may include one or more of a 30 minute time period, a 45 minute time period, a one hour time period, a two hour time period and a 6 hour time period. While exemplary predefined time periods are provided herein, within the scope of the present invention, any suitable predefined time period may be employed as may be sufficient to be used for glucose trend determination and/or therapy related determinations (such as, for example, modification of existing basal profiles, calculation of temporary basal profile, or determination of a bolus amount).

Referring back to FIG. 3, the consecutive glucose levels received over the predefined time period in one embodiment may not be entirely consecutive due to, for example, data transmission errors and/or one or more of potential failure modes associated with data transmission or processing. As such, in one embodiment of the present invention, there is provided a predetermined margin of error for the received real time glucose data such that, a given number of data points associated with glucose levels which are erroneous or alternatively, not received from the glucose sensor, may be ignored or discarded.

Referring back to FIG. 3, upon receiving the predetermined number of glucose levels over a predefined time period, the glucose trend information based on the received glucose levels is updated (320). For example, in one embodiment, the glucose trend information estimating the rate of change of the glucose levels may be determined, and based upon which the projected level of glucose may be calculated. Indeed, in one embodiment, the glucose trend information may be configured to provide extrapolated glucose level information associated with the glucose level movement based on the real time glucose data received from the glucose sensor. That is, in one embodiment, the real time glucose levels monitored are used to determine the rate at which the glucose levels is either increasing or decreasing (or remaining substantially stable at a given level). Based on such information and over a predetermined time period, a glucose projected information may be determined.

Referring again to FIG. 3, the therapy related parameters associated with the monitored real time glucose levels is updated (330). That is, in one embodiment, one or more insulin therapy related parameters of an insulin pump such as including, but not limited to, insulin on board information associated with the fluid delivery device 120 (FIG. 1), insulin sensitivity level of the patient 130 (FIG. 1), insulin to carbohydrate ratio, and insulin absorption rate. Thereafter, in one embodiment, one or more modifications to the current therapy profile are determined (340). That is, in one embodiment of the present invention, one or more current basal profiles, calculated bolus levels, temporary basal profiles, and/or any other suitable pre-programmed insulin delivery profiles stored in the fluid delivery device 120 (FIG. 1) for example, are retrieved and analyzed based on one or more of the received real time glucose levels, the updated glucose trend information, and the updated therapy related parameters.

Referring back to FIG. 3, after determining one or more modifications to the therapy profiles, the modified one or more therapy profiles is generated and output to the patient 130 (FIG. 1) (350) so that the patient 130 may select, store and/or ignore the one or more modified therapy profiles based on one or more of the monitored real time glucose values, updated glucose trend information, and updated therapy related parameters.

For example, in one embodiment, the patient 130 may be provided with a recommended temporary basal profile based on the monitored real time glucose levels over a predetermined time period as well as the current basal profile which is executed by the fluid delivery device 120 (FIG. 1) to deliver a predetermined level of insulin to the patient 130 (FIG. 1). Alternatively, the patient 130 in a further embodiment may be provided with one or more additional recommended actions for selection as the patient sees suitable to enhance the insulin therapy based on the real time monitored glucose levels. For example, the patient may be provided with a recommended correction bolus level based on the real time monitored glucose levels and the current basal profile in conjunction with, for example, the patient's insulin sensitivity and/or insulin on board information.

In this manner, in one embodiment of the present invention, based on real time monitored glucose levels, the patient may be provided with on-going, real time insulin therapy options and modifications to the pre-programmed insulin delivery basal profiles so as to improve upon the initially programmed therapy profiles based on the monitored real time glucose data.

Figure 4:
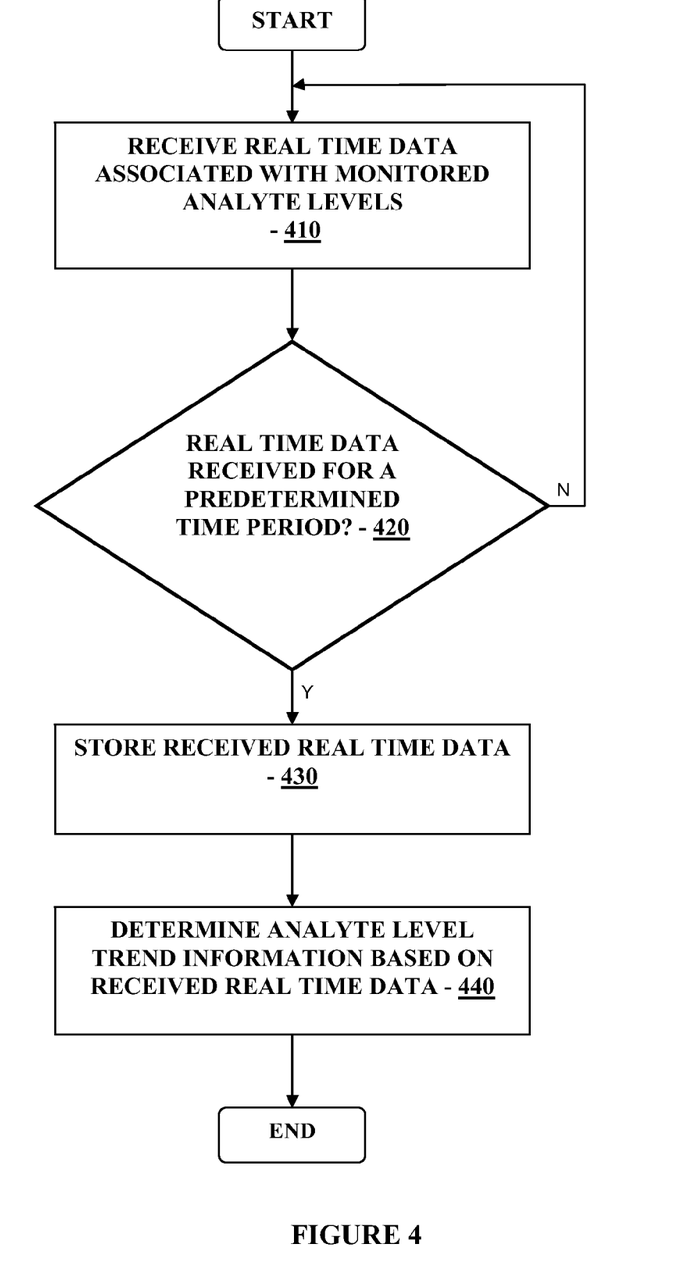
FIG. 4 is a flowchart illustrating an analyte trend information updating procedure based on real time monitored analyte levels in accordance with one embodiment of the present invention.

FIG. 4 is a flowchart illustrating analyte trend information updating procedure based on real time monitored analyte levels in accordance with one embodiment of the present invention. Referring to FIG. 4, in one embodiment, real time data associated with monitored analyte levels is received (410). Thereafter it is determined whether the real time data has been received for a predetermined time period (420). If it is determined that the real time data has not been received for at least the predetermined time period, then the routine continues to receive the real time data associated with the monitored analyte levels such as glucose levels.

On the other hand, referring back to FIG. 4, if it is determined that the real time data associated with the monitored analyte levels have been received for the predetermined time period (for example, as described above in conjunction with FIG. 3), then, the received real time data associated with the monitored analyte levels is stored (430). Thereafter, analyte level trend information is determined based on the received real time data associated with the monitored analyte levels (440).

For example, in one embodiment, the real time data associated with the monitored analyte levels is analyzed and an extrapolation of the data based on the rate of change of the monitored analyte levels is determined. That is, the real time data associated with the monitored analyte levels is used to determined the rate at which the monitored analyte level changed over the predetermined time period, and accordingly, a trend information is determined based on, for example, the determined rate at which the monitored analyte level changed over the predetermined time period.

In a further embodiment, the trend information based on the real time data associated with the monitored analyte levels may be dynamically modified and continuously updated based on the received real time data associated with the monitored analyte levels for one or more predetermined time periods. As such, in one embodiment, the trend information may be configured to dynamically change and be updated continuously based on the received real time data associated with the monitored analyte levels.

Figure 5:
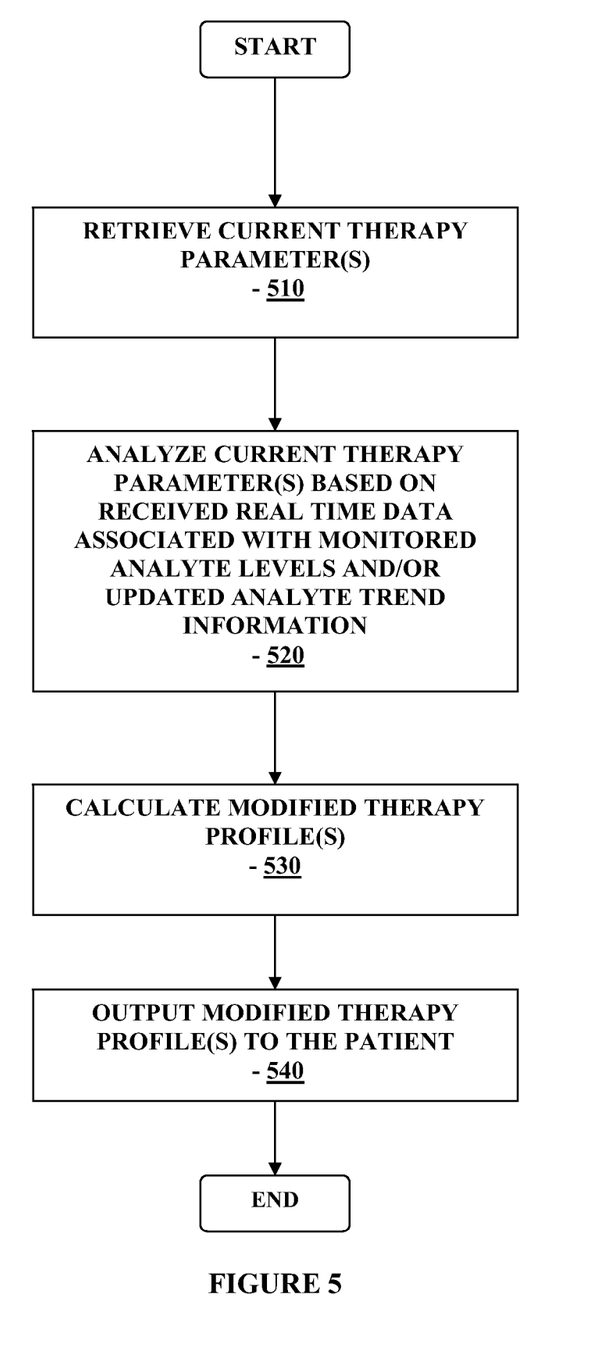
FIG. 5 is a flowchart illustrating a modified therapy management procedure based on real time monitored analyte levels in accordance with one embodiment of the present invention.

FIG. 5 is a flowchart illustrating modified therapy management procedure based on real time monitored analyte levels in accordance with one embodiment of the present invention. Referring to FIG. 5, in one embodiment, the current therapy parameters are retrieved (510) and, the retrieved current therapy parameters are analyzed based on the received real time data associated with the monitored analyte levels and/or updated analyte trend information (520). For example, one or more preprogrammed basal profiles, correction bolus, carbohydrate bolus, temporary basal and associated parameters are retrieved and analyzed based on, for example, the received real time data associated with the monitored analyte levels and/or updated analyte trend information, and further, factoring in the insulin sensitivity of the patient as well as insulin on board information.

Referring to FIG. 5, based upon the analysis of the current therapy parameters, one or more modified therapy profiles are calculated (530). That is, based upon the real time glucose levels monitored by the analyte monitoring system 110 (FIG. 1), a modification or adjustment to the pre-programmed basal profiles of the fluid delivery device 120 (FIG. 1) may be determined, and the modified therapy profiles are output to the patient 130 (FIG. 1) (540). That is, the modification or adjustment to the pre-programmed basal profiles may be provided to the patient for review and/or execution to implement the recommended modification or adjustment to the pre-programmed basal profiles.

In this manner, the patient may be provided with one or more adjustments to the existing or current basal profiles or any other pre-programmed therapy profiles based on continuously monitored physiological levels of the patient such as analyte levels of the patient. Indeed, in one embodiment of the present invention, using continuously monitored glucose levels of the patient, modification or adjustment to the pre-programmed basal profiles may be calculated and provided to the patient for review and implementation as desired by the patient. In this manner, for example, a diabetic patient may improve the insulin therapy management and control.

Within the scope of the present invention, the processes and routines described in conjunction with FIGS. 3-5 may be performed by the analyte monitoring system 110 (FIG. 1) and/or the fluid delivery device 120 (FIG. 1). Furthermore, the output of information associated with the modified therapy parameters, trend information, and/or real time data associated with the monitored analyte levels may be displayed on a display unit of the receiver of the analyte monitoring system 110 (FIG. 1), or the infusion device display of the fluid delivery device 120 (FIG. 1) or both. Alternatively, one or more such information may be output to the patient audibly as sound signal output.

In this manner, in accordance with the various embodiments of the present invention, there are provided methods and system for providing information associated with the direction and rate of change of analyte (e.g., glucose) levels for determination of, for example, bolus or basal rate change recommendations, for comparing expected glucose level changes to actual real time glucose level changes to update, for example, insulin sensitivity factor in an ongoing basis, and for automatically confirming the monitored glucose values within a preset time period (e.g., 30 minutes) after insulin therapy initiation to determine whether the initiated therapy is having the intended therapeutic effect.

Indeed, in accordance with the various embodiments of the present invention, the use of glucose trend information in insulin delivery rate determinations provides for a more accurate insulin dosing and may lead to a decrease in hypoglycemic events and improved HbA1Cs.

Accordingly, a method in one embodiment of the present invention includes receiving data associated with monitored analyte related levels for a predetermined time period substantially in real time, retrieving one or more therapy profiles associated with the monitored analyte related levels, generating one or more modifications to the retrieved one or more therapy profiles based on the data associated with the monitored analyte related levels.

The method may further include displaying the generated one or more modifications to the retrieved one or more therapy profiles.

In one aspect, the generated one or more modifications to the retrieved one or more therapy profiles may be displayed as one or more of an alphanumeric output display, a graphical output display, an icon display, a video output display, a color display or an illumination display.

In a further aspect, the predetermined time period may include a time period between 15 minutes and six hours.

The one or more therapy profiles in yet another aspect may include a basal profile, a correction bolus, a temporary basal profile, an insulin sensitivity, an insulin on board level, and an insulin absorption rate.

In still another aspect, retrieving the one or more therapy profiles associated with the monitored analyte related levels may include retrieving a current analyte rate of change information.

In yet still another aspect, generating the one or more modifications to the retrieved one or more therapy profiles may include determining a modified analyte rate of change information based on the received data associated with monitored analyte related levels.

Moreover, the method may further include generating an output alert based on the modified analyte rate of change information.

Still, the method may also include determining an analyte level projection information based on the modified analyte rate of change information.

A system for providing diabetes management in accordance with another embodiment of the present invention includes an interface unit, one or more processors coupled to the interface unit, a memory for storing instructions which, when executed by the one or more processors, causes the one or more processors to receive data associated with monitored analyte related levels for a predetermined time period substantially in real time, retrieve one or more therapy profiles associated with the monitored analyte related levels, and generate one or more modifications to the retrieved one or more therapy profiles based on the data associated with the monitored analyte related levels.

The interface unit may include an input unit and an output unit, the input unit configured to receive the one or more analyte related data, and the output unit configured to output the one or more of the generated modifications to the retrieved one or more therapy profiles.

The interface unit and the one or more processors in a further embodiment may be operatively coupled to one or more of a housing of an infusion device or a housing of an analyte monitoring system.

The infusion device may include one of an external insulin pump, an implantable insulin pump, an on-body patch pump, a pen-type injection device, an inhalable insulin delivery system, and a transdermal insulin delivery system.

The memory in a further aspect may be configured for storing instructions which, when executed by the one or more processors, causes the one or more processors to display the generated one or more modifications to the retrieved one or more therapy profiles.

Further, the memory may be configured for storing instructions which, when executed by the one or more processors, causes the one or more processors to display the generated one or more modifications to the retrieved one or more therapy profiles as one or more of an alphanumeric output display, a graphical output display, an icon display, a video output display, a color display or an illumination display.

In one aspect, the predetermined time period may include one of a time period between 15 minutes and six hours.

The one or more therapy profiles may include a basal profile, a correction bolus, a temporary basal profile, an insulin sensitivity, an insulin on board level, and an insulin absorption rate.

In another aspect, the memory may be further configured for storing instructions which, when executed by the one or more processors, causes the one or more processors to retrieve a current analyte rate of change information.

In still another aspect, the memory may be further configured for storing instructions which, when executed by the one or more processors, causes the one or more processors to determine a modified analyte rate of change information based on the received data associated with monitored analyte related levels.

Additionally, in yet still another aspect, the memory may be further configured for storing instructions which, when executed by the one or more processors, causes the one or more processors to generate an output alert based on the modified analyte rate of change information.

Further, the memory may be further configured for storing instructions which, when executed by the one or more processors, causes the one or more processors to determine an analyte level projection information based on the modified analyte rate of change information.

A system for providing diabetes management in accordance with yet another embodiment of the present invention includes an analyte monitoring system configured to monitor analyte related levels of a patient substantially in real time, a medication delivery unit operatively for wirelessly receiving data associated with the monitored analyte level of the patient substantially in real time from the analyte monitoring system, a data processing unit operatively coupled to the one or more of the analyte monitoring system or the medication delivery unit, the data processing unit configured to retrieve one or more therapy profiles associated with the monitored analyte related levels, and generate one or more modifications to the retrieved one or more therapy profiles based on the data associated with the monitored analyte related levels.

In one aspect, the analyte monitoring system may be configured to wirelessly communicate with the medication delivery unit over a radio frequency (RF) communication link, a Bluetooth® communication link, an Infrared communication link, or a local area network (LAN).

The various processes described above including the processes performed by the processor 210 in the software application execution environment in the fluid delivery device 120 as well as any other suitable or similar processing units embodied in the analyte monitoring system 110 and the remote terminal 140, including the processes and routines described in conjunction with FIGS. 3-5, may be embodied as computer programs developed using an object oriented language that allows the modeling of complex systems with modular objects to create abstractions that are representative of real world, physical objects and their interrelationships. The software required to carry out the inventive process, which may be stored in the memory unit 240 (or similar storage devices in the analyte monitoring system 110 and the remote terminal 140) of the processor 210, may be developed by a person of ordinary skill in the art and may include one or more computer program products.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A method, comprising:
    determining, using one or more processors, a rate of change of a monitored glucose level for a predetermined time period;
    extrapolating, using the one or more processors, a projected glucose level based on the determined rate of change of the monitored glucose level;
    determining, using the one or more processors, after insulin therapy initiation, whether the insulin therapy is having an intended therapeutic result;
    generating, using the one or more processors, a modification to a therapy profile associated with the insulin therapy based on data associated with the monitored glucose level; and
    updating, using the one or more processors, an insulin sensitivity factor on an ongoing basis based at least in part on a comparison of the projected glucose level with the monitored glucose level.

2. The method of claim 1, further including displaying the generated modification to the therapy profile.

3. The method of claim 2, wherein the generated modification to the therapy profile is displayed as one or more of an alphanumeric output display, a graphical output display, an icon display, a video output display, a color display or an illumination display.

4. The method of claim 1, wherein the therapy profile includes one or more of a basal profile, a correction bolus, a temporary basal profile, an insulin sensitivity, an insulin on board level, or an insulin absorption rate.

5. The method of claim 1, wherein generating the modification to the therapy profile associated with the monitored glucose level includes retrieving a current glucose rate of change information.

6. The method of claim 5, wherein generating the modification to the therapy profile includes determining a modified glucose rate of change information based on the data associated with the monitored glucose level.

7. The method of claim 6, further including generating an output alert based on the modified glucose rate of change information.

8. The method of claim 6, further including determining a glucose level projection information based on the modified glucose rate of change information.

9. A system, comprising:
an interface unit;
one or more processors coupled to the interface unit; and
a memory for storing instructions which, when executed by the one or more processors, causes the one or more processors to determine a rate of change of a monitored glucose level for a predetermined time period, to extrapolate a projected glucose level based on the determined rate of change of the monitored glucose level, to determine after insulin therapy initiation whether the insulin therapy is having an intended therapeutic result, to generate a modification to a therapy profile associated with the insulin therapy based on data associated with the monitored glucose level, and to update an insulin sensitivity factor on an ongoing basis based at least in part on a comparison of the projected glucose level with the monitored glucose level.

10. The system of claim 9, wherein the interface unit includes an input unit and an output unit, the input unit configured to receive the data associated with the monitored glucose level, and the output unit configured to output the generated modification to the therapy profile.

11. The system of claim 9, wherein the interface unit and the one or more processors are operatively coupled to one or more of a housing of an infusion device or a housing of an analyte monitoring system.

12. The system of claim 9, wherein the memory is further configured for storing instructions which, when executed by the one or more processors, causes the one or more processors to display the generated modification to the therapy profile.

13. The system of claim 12, wherein when the memory is configured for storing instructions which, when executed by the one or more processors, causes the one or more processors to display the generated modification to the therapy profile as one or more of an alphanumeric output display, a graphical output display, an icon display, a video output display, a color display or an illumination display.

14. The system of claim 9, wherein the therapy profile includes one or more of a basal profile, a correction bolus, a temporary basal profile, an insulin sensitivity, an insulin on board level, or an insulin absorption rate.

15. The system of claim 9, wherein the memory is further configured for storing instructions which, when executed by the one or more processors, causes the one or more processors to retrieve a current glucose rate of change information.

16. The system of claim 15, wherein the memory is further configured for storing instructions which, when executed by the one or more processors, causes the one or more processors to determine a modified glucose rate of change information based on the data associated with the monitored glucose level.

17. The system of claim 16, wherein the memory is further configured for storing instructions which, when executed by the one or more processors, causes the one or more processors to generate an output alert based on the modified glucose rate of change information.

18. The system of claim 16, wherein the memory is further configured for storing instructions which, when executed by the one or more processors, causes the one or more processors to determine a glucose level projection information based on the modified glucose rate of change information.

* * * * *